（12） United States Patent
Han et al.

(10) Patent No.: US 8,623,192 B2
(45) Date of Patent: Jan. 7, 2014

(54) HIGH RESOLUTION FOCUSING AND SEPARATION OF PROTEINS IN NANOFLUIDIC CHANNELS

(75) Inventors: Sang M. Han, Albuquerque, NM (US); Youn-Jin Oh, San Ramon, CA (US); Cornelius Ivory, Pullman, WA (US)

(73) Assignee: STC.UNM, Albuquerque, NM (US)

( * ) Notice: Subject to any disclaimer, the term of this patent is extended or adjusted under 35 U.S.C. 154(b) by 161 days.

(21) Appl. No.: 13/125,096

(22) PCT Filed: Oct. 20, 2009

(86) PCT No.: PCT/US2009/061314
§ 371 (c)(1),
(2), (4) Date: Apr. 20, 2011

(87) PCT Pub. No.: WO2010/048173
PCT Pub. Date: Apr. 29, 2010

(65) Prior Publication Data
US 2011/0192724 A1    Aug. 11, 2011

Related U.S. Application Data

(60) Provisional application No. 61/106,648, filed on Oct. 20, 2008.

(51) Int. Cl.
*B03C 5/02*    (2006.01)

(52) U.S. Cl.
USPC ........... 204/547; 204/450; 204/470; 204/600; 204/643; 204/645

(58) Field of Classification Search
USPC ................. 204/450–470, 547–550, 600–621, 204/643–645
See application file for complete search history.

(56) References Cited

U.S. PATENT DOCUMENTS

| | | | |
|---|---|---|---|
| 6,833,061 B1 * | 12/2004 | Fuhr et al. ...................... | 204/548 |
| 7,200,311 B1 | 4/2007 | Han | |
| 2002/0058332 A1 * | 5/2002 | Quake et al. ................ | 435/288.3 |
| 2003/0127329 A1 | 7/2003 | DeVoe et al. | |
| 2006/0054504 A1 | 3/2006 | Lee et al. | |
| 2006/0169587 A1 | 8/2006 | Lopez et al. | |
| 2008/0083621 A1 * | 4/2008 | Sideris ......................... | 204/450 |
| 2008/0251382 A1 * | 10/2008 | Han et al. ...................... | 204/554 |

OTHER PUBLICATIONS

Patent Cooperation Treaty, International Search Report, International Application No. PCT/US2009/061314, May 12, 2010, 3 pages.
Oh, Youn-Jin et al., "Monitoring FET flow control and wail adsorption of charged fluorescent dye molecules in nanochanneis integrated into a multiple internal reflection infrared waveguide," The Royal Society of Chemistry, 2008, 8, 251-258.
Bottenus, Danny et al., "Experimentally and theoretically observed native pH shifts in a nanochannel array," The Royal Society of Chemistry, 2009, 9, 219-231.

(Continued)

*Primary Examiner* — Keith Hendricks
*Assistant Examiner* — Bach Dinh
(74) *Attorney, Agent, or Firm* — MH2 Technology Law Group, LLP

(57) ABSTRACT

Exemplary embodiments provide systems and methods for concentrating, focusing and/or separating proteins using nanofluidic channels and/or their arrays. In embodiments, low-abundance proteins can be focused and separated with high resolution using separation techniques including isoelectric focusing (IEF), and/or dynamic field gradient focusing (DFGF) in combination with nanofluidic channels and/or multi-gate nanofluidic field-effect-transistors (FETs).

14 Claims, 4 Drawing Sheets

(56) References Cited

OTHER PUBLICATIONS

Oh, Youn-Jin et al., "Impact of leakage current and electrolysis on FET flow control and pH changes in nanofluidic channels," The Royal Society of Chemistry, 2009, 9, 1609-1617.

Oh, Youn-Jin et al., "Effect of wall-molecule interactions on electrokinetio transport of charged molecules in nanafluidic channels during FET flow control," The Royal Society of Chemistry, 2009, 9, 1601-1608.

* cited by examiner

200

220

HIGH RESOLUTION FOCUSING AND SEPARATION OF PROTEINS IN NANOFLUIDIC CHANNELS

RELATED APPLICATIONS

This application claims priority from U.S. Provisional Patent Application Ser. No. 61/106,848, filed Oct. 20, 2008, which is hereby incorporated by reference in its entirety.

GOVERNMENT RIGHTS

This invention was made with Government support under Contract No. CTS-0404124 awarded by the National Science Foundation. The U.S. Government has certain rights in this invention.

DESCRIPTION OF THE INVENTION

1. Field of the Invention

This invention relates generally to protein analysis and, more particularly, to systems and methods for focusing and separating proteins using nanofluidic channels.

2. Background of the Invention

It is desirable to concentrate, separate, and characterize low-abundance proteins with high resolution for diagnostic detection of trace biomarkers and treatment of human diseases.

Conventional tools for protein separation include polyacrylamide gel electrophoresis (PAGE) apparatus, which is commercially available and often used in combination with isoelectric focusing (IEF). Notwithstanding its widespread use, a number of limitations exist for the PAGE technique, such as long separation times, large amounts of required samples, low reproducibility, breakdowns under high electric field, and low dynamic ranges.

To overcome these limitations of the conventional PAGE technique, a number of new separation platforms have emerged using microfluidic and nanofluidic channels. For example, microfluidic devices enable rapid separation and analysis, cost saving for analytes and device fabrication, and high resolution. More recently, nanofluidic separation platforms have been proposed to improve the efficiency of protein analysis and to explore novel separation techniques using unique characteristics of nanofluidic channels.

However, successful high-resolution protein separations in nanofluidic channels have not been reported to date. For instance, there is no available system or apparatus that is adapted to establish a stable pH gradient without the use of conventional ampholytes to allow isoelectric focusing (IEF). Further, there is no available technology that allows for the dynamic, real-time manipulation of pH gradient and electric field gradient along the channels, while simultaneously controlling electroosmosis and electrophoresis, to achieve IEF and/or dynamic field gradient focusing (DFGF). Lastly, no existing technologies possess desirable resolution for low-abundance protein separations.

Thus, there is a need to overcome these and other problems of the prior art and to provide systems and methods for high-resolution focusing and separation of proteins using nanofluidic channels.

SUMMARY OF THE INVENTION

According to various embodiments, the present teachings include a method for focusing proteins. In order to focus proteins, a plurality of nanofluidic channels can be provided with each nanofluidic channel having a width or a depth of about 1000 nm or less. A protein mixture solution that contains a plurality of proteins can then be introduced into the nanofluidic channels, followed by applying an electric potential to a length of the protein mixture solution. A longitudinal electric field along the nanofluidic channels can then be generated to focus and/or separate the plurality of proteins in the protein mixture solution.

According to various embodiments, the present teachings also include a system for focusing proteins. The system can include a nanofluidic array disposed in a substrate material. The nanofluidic array can include a plurality of nanofluidic channels with each nanofluidic channel having a width or depth of about 1000 nm or less, wherein a protein mixture solution is able to flow within the nanofluidic array through each nanofluidic channel. The system for focusing proteins can also include a power supply for applying an electric potential to a length of the protein mixture solution along each nanofluidic channel to form a longitudinal electric field. The system for focusing proteins can further include a multi-gate nanofluidic field-effect-transistor (FET) configuration that includes a plurality of gates spaced along the nanofluidic channels to dynamically control at least one of a pH gradient, an electric field gradient, and electrokinetic transport of the plurality of proteins in nanofluidic channels.

According to various embodiments, the present teachings further include a method for focusing proteins. In this method, a nanofluidic device can be used and can include at least one nanofluidic array and a plurality of end wells connected to at least one nanofluidic array for a liquid to flow through. Each nanofluidic array of the device can include a plurality of nanofluidic channels with each channel having a width or a depth of less than about 1000 nm. A protein mixture solution that includes a plurality of proteins in a buffer solution can then be introduced into one of the plurality of end wells. An electrode can then contact with the protein mixture solution in the end well for applying an electric potential to generate a longitudinal electric field along the nanofluidic channels. In embodiments, the application of the electric potential can result in one or more focused protein bands with each focused protein band corresponding to a protein of the plurality of proteins in the protein mixture solution. In embodiments, a multi-gate nanofluidic field-effect-transistor (FET) can be configured having a plurality of gates spaced along the nanofluidic channels to dynamically control at least one of a pH gradient, an electric field gradient and electrokinetic transport of the plurality of proteins in the protein mixture solution.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Exemplary embodiments provide systems and methods for focusing and/or separating proteins using nanofluidic channels and/or arrays of nanofluidic channels. The disclosed nanofluidic apparatus, systems and methods can provide a versatile platform to separate proteins, for example low-abundance proteins, with high resolution, using separation techniques including for example, isoelectric focusing (IEF), dynamic field gradient focusing (DFGF) and/or a combination thereof. In embodiments, a control scheme using multi-gate nanofluidic field-effect-transistors (FETs) can be combined with the disclosed nanofluidic technique.

In embodiments, a stable pH gradient can be established in nanofluidic channels without the use of ampholytes upon an application of a longitudinal electric field to the protein mixture solution in the nanofluidic channels, thereby allowing for isoelectric focusing (IEF). In embodiments, the balance between electroosmosis and electrophoresis (e.g., electrophoretic mobility vs. counter flow buffer) can also be controlled dynamically in nanofluidic channels to achieve dynamic field gradient focusing (DFGF). In embodiments, IEF and DFGF can work simultaneously in the same system to concentrate, focus and/or separate proteins.

Various embodiments therefore allow high resolution IEF and/or DFGF and separation of proteins using the nanochannel array, in combination with electroosmosis, electrophoresis, natural pH gradient, and different mobility of proteins. As compared with conventional techniques, the disclosed systems and methods do not use ampholytes to build up the pH gradient, do not use multi buffer ionic species to induce diffusion potential, and do not use surface treatment to enhance isoelectric focusing. The disclosed systems and methods, however, can use low electric potential to achieve isoelectric focusing of proteins. The low electric potential for IEF can be, for example, about 5 V or less or in embodiments, about 3 V or less.

Figure 1:
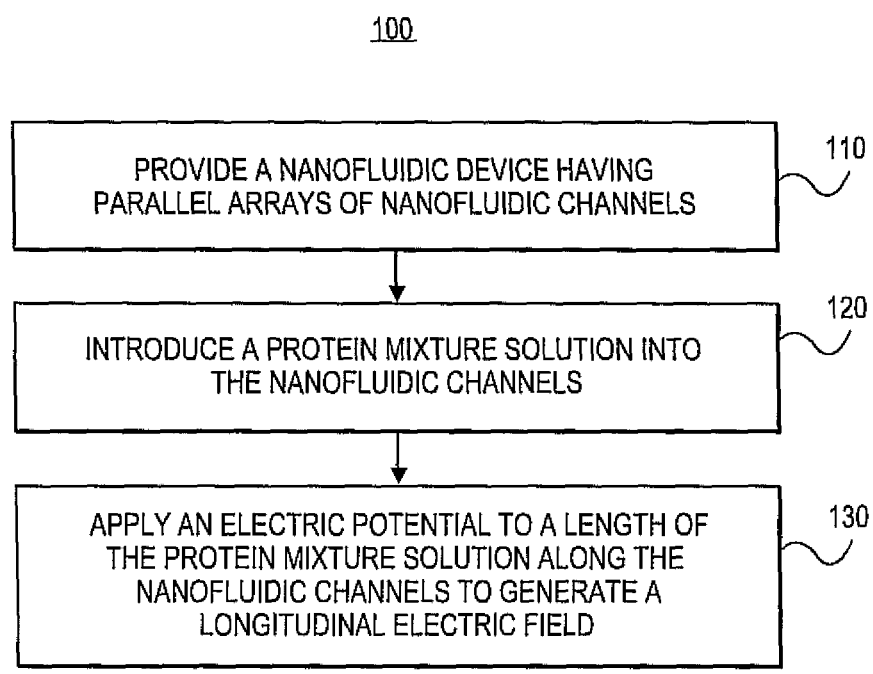
FIG. 1 depicts an exemplary method for focusing and/or separating proteins in accordance with various embodiments of the present teachings.

FIG. 1 depicts an exemplary method 100 for focusing and/or separating proteins in accordance with various embodiments of the present teachings. FIGS. 2A-2E depict a schematic of the exemplary nanofluidic device and system to conduct high-resolution focusing and separation of proteins within nanochannels in accordance with various embodiments of the present teachings.

Figure 2A:
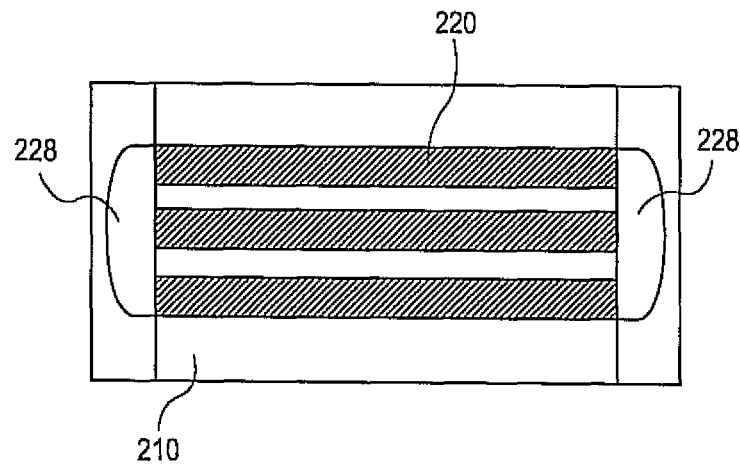
FIGS. 2A-2B depict portions of an exemplary nanofluidic device in accordance with various embodiments of the present teachings.
Figure 2B:
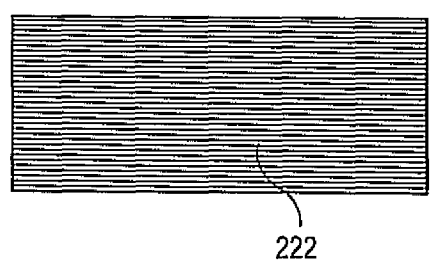
Figure 2C:
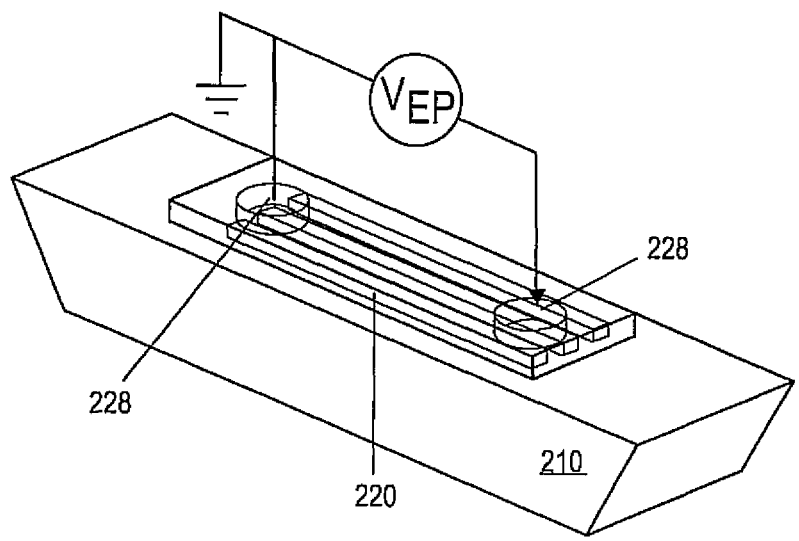
FIG. 2C depicts an exemplary nanofluidic system in accordance with various embodiments of the present teachings.
Figure 2D:
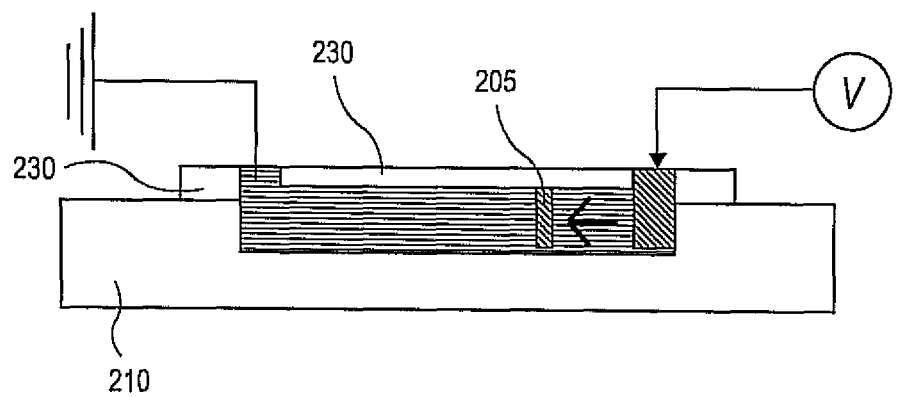
FIG. 2D depicts an exemplary nanofluidic channel during protein focusing in accordance with various embodiments of the present teachings.
Figure 2E:
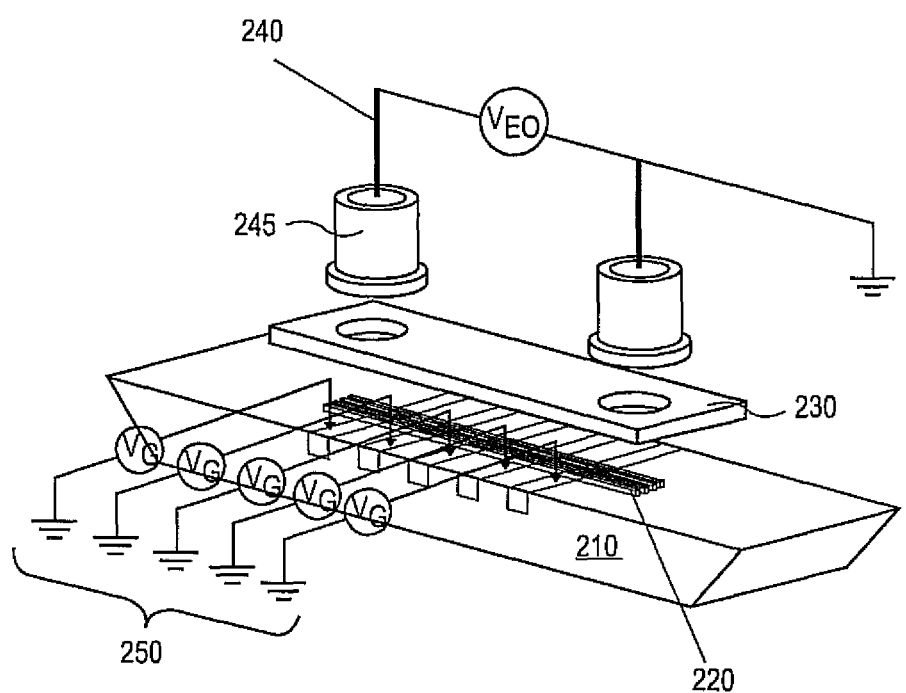
FIG. 2E depicts another exemplary nanofluidic system in accordance with various embodiments of the present teachings.

Specifically, FIG. 2A depicts a schematic top view of a portion of an exemplary nanofluidic device 200; FIG. 2B depicts a close-up schematic of an exemplary nanofluidic array 220 of the device 200; FIG. 2C depicts an exemplary system 200C for focusing and/or separating proteins using the device 200; FIG. 2D depicts a cross-sectional schematic of an exemplary nanochannel when used to focus/separate proteins; and FIG. 2E depicts another exemplary system 200E using a control scheme of multi-gate nanofluidic FETs (field-effect-transistors) in accordance with various embodiments of the present teachings.

Note that although the method 100 will be described in reference to FIGS. 2A-2E for illustrative purposes, the process of method 100 is not limited to the structures shown in FIGS. 2A-2E. In addition, while the method 100 of FIG. 1 is illustrated and described below as a series of acts or events, it will be appreciated that the present teachings are not limited by the illustrated ordering of such acts or events. For example, some acts may occur in different orders and/or concurrently with other acts or events apart from those illustrated and/or described herein. Also, not all illustrated steps may be required to implement a methodology in accordance with one or more aspects or embodiments of the present invention. Further, one or more of the acts depicted herein may be carried out in one or more separate acts and/or phases.

At 110 of FIG. 1, a nanofluidic device 200 can be provided as shown in FIGS. 2A-2E. The device 200 can include one or more nanochannel arrays 220 formed in a substrate 210 (see FIGS. 2C-2E). In embodiments, the one or more nanochannel arrays 220 can be configured to be parallel. The substrate 210 can be made of any suitable substrate material including for example silicon, a III-V substrate, ceramic, glass, plastic, etc. In embodiments, the substrate material can be a semiconducting material including silicon and/or germanium.

Each array 220 can include a plurality of nanochannels 222 (or nanofluidic channels). In embodiments, each array 220 can have a desired number of nanofluidic channels 222, for example, about 2 to about $10^8$. In embodiments, the nanofluidic channels 222 can be configured to be substantially parallel. In certain embodiments, each array 220 can include from about 120 to about 180 parallel nanochannels, although other number of parallel channels can also be used for the disclosed nanofluidic device.

In embodiments, the nanochannel 222 can have at least one minor dimension, for example, depth of about 1000 nanometers or less, in embodiments, of about 500 nanometers or less. In an exemplary embodiment, the nanochannel 222 can have at least one minor dimension, for example, width of about 1000 nanometers or less, in embodiments, ranging from about 15 nanometers to about 100 nanometers. In embodiments, the nanochannel 222 can have one of the width and the depth of about 1000 nm or less. In embodiments, the nanochannel 222 can have a length of at least about 100 micrometers, for example, ranging from about 100 micrometers to about 2 centimeters or to about 10 centimeters.

The nanochannels 222 and their arrays 220 can be fabricated using suitable semiconductor fabrication processes. For example, the nanochannels 222 can be formed in the substrate 210 by a lithography process, such as interferometric lithography (IL) and an etching process, such as a plasma etching process of the substrate 210. In embodiments, an electrically insulating layer (not illustrated) can be formed on substrate wall surfaces of each nanochannel 222. The insulating layer can be formed of, for example, $SiO_2$, $Si_3N_4$, $Al_2O_3$, and/or $TiO_2$. In an exemplary embodiment, a thermally grown $SiO_2$ layer having a thickness of, for example, about 100 nm or less, can be used as an electrically insulating layer between the substrate nanochannel walls and the fluid flowing through each channel.

In embodiments, the device 200 can include a plurality of end wells 228. The end wells 228 can be connected with each nanochannel 222 and/or nanochannel array 220, wherein, for example, liquid can pass through the nanochannels 222 from the end well 228 by capillary force. In embodiments, the end wells 228 can be used as liquid or solution reservoirs for introducing and storing the liquid or solution.

In embodiments, as shown in FIGS. 2D-2E, the nanochannels 222 of the nanofluidic device 200 can be sealed with an optically transparent material 230, for example, a Pyrex cover, which can be bonded onto the substrate 210, for example, by anodic bonding to form the nanofluidic device 200. In embodiments, the optically transparent material 230 can also include, for example, glass, quartz, polydimethylsiloxane (PDMS), and/or plastic.

In various exemplary embodiments, the nanochannel 222 can have a width on the order of a thickness of electric double layer (EDL). Due to this dimensional comparability, the EDLs can overlap in nanofluidic channels, giving rise to unique characteristics that are not readily achievable in conventional microfluidic channels, but can be exploited for biomolecular separations. There can be many advantages provided by nanofluidic channels. For example, electroosmosis (EO) can be a dominant mechanism of molecular transport over electrophoresis (EP) and can be controlled by modulating the $\zeta$-potential with an externally applied electric potential (V) to the nanochannel walls. In another example, electrostatic interaction of charged biomolecules and nanochannel walls can be more pronounced than in microfluidic channels and can allow one to control the electrokinetic mobility of charged molecules much more effectively than in microchannels. Additionally, differently sized molecules, such as DNA and protein molecules, can be separated using the nanoscale sieving structure, where surface charges can be controlled.

At 120 of FIG. 1, a protein-containing solution or a protein mixture solution can be introduced into the nanofluidic channels 222 and/or their arrays 220. For example, the protein mixture solution can be introduced into one of the end wells 228 and can further fill the nanofluidic channels 222 and/or their arrays 220 by capillary force or by electroosmosis.

In embodiments, prior to introducing the protein mixture solution, both the end wells 228 and/or the nanochannels 222/arrays 220 can first be filled with a buffer solution, for example, by capillary force. In embodiments, the buffer solution can be selected according to the specification of particular proteins and can be used to dilute proteins. For example, the buffer solution can have a pH ranging from about 2 to about 10 and an ionic strength ranging from about 0.1 mM to about 100 mM. Depending on the proteins used, other pH ranges and ionic strengths can also be included in various embodiments.

The buffer solution can be equilibrated for a period of time in order to reach equilibrium of materials, for example, between the buffer solution and the nanochannel walls that include a material of, for example, $SiO_2$. Depending on the system, the equilibrium time can be determined by IR absorbance spectra over time. For example, after a period of time, if no noticeable changes are detected by IR absorbance spectra, the buffer solution in the nanochannels 222 or the nanoarrays 220 can be assumed to be equilibrated. In embodiments, the equilibrium time can range from about 10 minutes to about 30 minutes, although other equilibrium time can be used depending on the material systems.

In embodiments, the substrate 210 can have beveled edges on both ends that can allow IR access through the substrate and perform multiple internal reflection Fourier transform infrared (MIR-FTIR) spectroscopy to probe molecules in the nanochannels 222. In embodiments, the IR technique used to monitor the system equilibrium can include the IR technique as described in U.S. Pat. No. 7,200,311, entitled "Surface Corrugation on Internal Reflection Infrared Waveguide for Enhanced Detection Sensitivity and Selectivity," which is hereby incorporated by reference in its entirety.

In embodiments, the protein mixture solution can have a protein concentration ranging from a high concentration on the order of millimolar to a low concentration on the order of attomolar. For example, the protein mixture solution can have a protein concentration of about 1 millimolar or less. In embodiments, the protein mixture buffer solution can have low abundance proteins with concentration on the order of picomolar. Such low abundance proteins can be concentrated, focused, separated and/or analyzed by using the nanofluidic devices and systems as described herein.

At 130 of FIG. 1, an electric potential can be applied to a length of the exemplary protein mixture solution in the nanofluidic channels 222 or the nanofluidic arrays 220 to generate a longitudinal electric field along the nanofluidic channels. In embodiments, any suitable power supply as known to one of ordinary skill in the art can be used to apply the electric potential.

In embodiments, suitable electrodes (see 240 in FIG. 2E) can be used to contact the protein mixture solution for the application of electric potential. For example, any conductive material, including any metal-containing material or other known electrodes can be used to contact with the protein mixture solution in the nanofluidic channels 222.

In embodiments, two electrodes (see 240 in FIG. 2E) can be used to apply electric potential through the protein mixture solution and can be spaced apart from each other to form the longitudinal electric field there-between (see FIGS. 2C-2E), In exemplary embodiments, the electrodes can contact the protein mixture solution in the end wells 228 through connectors 245, wherein the center-to-center spacing between the two end wells 228 can range from about 100 μm to about 2 cm or to about 10 cm.

After the electrodes are configured to contact the protein mixture solution that contains one or more proteins, the electric potential can then be applied to generate a longitudinal electric field. The longitudinal electric field can result in one or more focused protein bands 205.

In an exemplary embodiment, as shown in FIGS. 2C-2E, a negative bias ($V_{EP}$) can be applied to one end well 228, and the opposite side end well 228 can be grounded to induce an electrokinetic flow. In embodiments, the longitudinal electric field (E) along the nanochannels 222 or the arrays 220 can induce an electroosmotic (EO) flow typically with opposing electrophoresis (EP) for negatively charged molecules such as protein molecules that are negatively charged. Because water electrolysis occurs at both electrodes as electric potential is applied, a pH gradient can be established along the longitudinal electric field, which is along the length of the nanochannels 222 or the arrays 220.

In various embodiments, as shown in FIG. 2E, a multi-gate nanofluidic FET control scheme 250 can be used in combination with the focusing/separating system of FIG. 2C. In an exemplary embodiment, a plurality of gates, for example, formed by highly doped regions of the substrate material such as Si, can be placed along the nanochannels. By locally applying additional electric potentials to the channel walls that encapsulate the protein mixture solution, local pH value and electrical potential in the solution contained in the nanochannels and adjacent to the gates can then be dynamically controlled. In this manner, varying electrical potentials, for example, gradient DC potentials, can be applied to the gates to dynamically control the pH gradient and electric field gradient in real time along the nanochannels. Further, in embodiments, the multi-gate nanofluidic FET control scheme 250 can allow an application and manipulation of the additional electric potentials to simultaneously control the electrokinetic transport of proteins (e.g., electroosmosis vs. electrophoresis) along the nanofluidic channels.

In embodiments, the multi-gate nanofluidic FET control scheme 250 can include the scheme described in U.S. patent application Ser. No. 11/184,540, entitled "Nanofluidics for Bioseparation and Analysis," which is hereby incorporated by reference in its entirety.

The protein bands 205 can then be focused with each focused band corresponding to at least one protein of the protein mixture solution and therefore to focus and/or separate the proteins. In embodiments, the focused protein band 205 (see FIG. 2D) can be statically focused for a period of time along the longitudinal electric field and then flow forward electrokinetically by electroosmosis/electrophoresis. In embodiments, the focused protein band 205 can be statically focused for a period of time, for example, ranging from about 5 minutes to about 30 minutes. In embodiments, the focused protein band 205 can have a high resolution, i.e., a narrow width of, for example about 100 μm or less.

In embodiments, formation of the protein band 205 and movement of the band 205 through the nanochannels 222 or the nanoarrays 220 can be controlled by controlling the application of the longitudinal electric potential and/or the electric potentials that applied to individual gates of the multi-gate nanofluidic FETs.

In one embodiment, the location of band formation can be controlled along the longitudinal electric field by increasing or decreasing the applied electric potential. For example, as observed in experiments, an increased electric potential can push or advance the proteins move further along the longitudinal electric field and can thus form a focused band even further from its original spot.

In one embodiment, the length of time for forming the focused protein band 205, i.e., from the time when the electric potential is applied to the time when the band forms, can be controlled by controlling the application of electric potential. For example, an increased (or decreased) electric potential can reduce (or increase) the band formation time. This is because the movement of protein bands can be determined by the equilibrium between electrophoresis and electroosmosis, wherein electroosmosis can be much more dominant than other forces such as electrophoresis, ion diffusion, and pH gradient effect in nanochannels having a nano-width of about 100 nm or less. The electric potential modulation can therefore govern the solution flow by electroosmosis in the early stage. That is, an increased (or decreased) electric potential can enhance (or weaken) the electroosmosis flow. In embodiments, as compared with conventional separation techniques, the disclosed systems and methods for focusing/separating proteins can form a focused band in high speed, for example, of about 1 minute or shorter. In a particular example, when focusing protein ovalbumin (OVA) using an electric potential of about −40V, the focused band formation time can be as short as about 10 seconds.

In one embodiment, the movement of proteins in the nanochannels can be controlled, for example, by controlling the amount and/or the direction of the applied electric potential. For example, proteins can be moved repeatably and continuously in both directions along the longitudinal electric field or along the length between the two electrodes through which electric potential can be applied. In an exemplary embodiment, proteins can move in an opposite direction along the longitudinal electric field by increasing or decreasing the electric potential applied. The changed potential can break the electrokinetic equilibrium that is previously formed by the previously applied electric potential. In embodiments, the amount of electric potential can be changed in an alternating fashion, in an increasing fashion or in a decreasing fashion so as to control the flowing directions of the proteins between the two electrodes for repeatable focusing and separation.

In embodiments, the electric potential can be a pre-determined electric potential depending on, for example, molecular weights of proteins in the protein mixture solution. In embodiments, a high molecular weight of proteins may require a high electric potential for the mobility of proteins. In exemplary embodiments, molecular weights of BSA (bovine serum albumin, MW~66,000) and OVA (ovalbumin, MW~45,000) can be 4 times smaller than those of RPE (r-phycoerythrin, MW~240,000) and APC (allophycocyanin, MW~104,000). In embodiments, BSA and OVA can then be highly controllable with a low-magnitude electric potential, for example, as low as $-5$ $V_{EP}$ due to their low molecular weights. In contrast, RPE and APC bands can appear at a high-magnitude electric potential, for example, with $V_{EP}>-60$ in magnitude.

In embodiments, various proteins can be concentrated, focused, separated and/or analyzed by using the systems and methods as described in FIGS. 1-2. The separation mobility of proteins can be determined by size (i.e., size exclusion) and/or molecular weight of proteins, electrostatic interaction of charged species in the protein mixture solution and electrodes (e.g., the applied electric potential that determines pH gradient generation), etc. Different electric mobilities of proteins can result in protein separation with proteins having different band formation times and band formation locations.

In embodiments, the systems and methods described herein can be used to focus and/or separate proteins for certain protein systems, for example, where proteins having same sign of charge but having sizes slightly different yet in the same size range are mixed in a solution. For example, APC and RPE are large proteins with net negative charges but slightly different in size. In another example, BSA and OVA are small proteins with net negative charges but slightly different in size.

In exemplary embodiments when the protein mixture includes proteins of OVA and BSA, OVA can be focused near the inlet end well of the nanochannel device and form a very sharp focused band, while BSA can be sharply focused further but close to the focused OVA band after a period of time.

As disclosed, the focused bands of exemplary BSA and OVA in the nanochannels and nanoarrays can be highly selective and very narrow as compared with other methods using microchannels or capillaries. Further, protein focusing and separation as disclosed herein can be achieved by applying a very low electric potential, for example, as low as 3.6 V. Note that, unlike conventional methods, no additional ampholytes nor special buffer ions are used to establish the pH gradient and to induce protein-focusing. Furthermore, the high-resolution protein focusing of BSA and OVA in nanochannels can be repeatable.

In this manner, the band formation and separation of proteins can be achieved by isoelectric focusing due to a natural longitudinal pH gradient along the nanochannels created by water electrolysis occurring on the electrodes 240 in the end wells 228, in conjunction with DFGF due to the force balance of electroosmosis/electrophoresis and ion concentration polarization.

EXAMPLES

Example 1

Nanofluidic Device and Characterizations

A nanofluidic separation matrix was fabricated and operated as described in *Lab on a Chip* 2009, entitled "Effect of Wall-Molecule Interactions on Electrokinetic Transport of Charged Molecules in Nanofluidic Channels during FET Flow Control;" in *Lab on a Chip* 2009, entitled "Impact of Leakage Current and Electrolysis on FET Flow Control and pH Changes in Nanofluidic Channels;" and in *Lab on a Chip* 2009, entitled "Experimentally and Theoretically Observed Native pH Shifts in a Nanochannel array;" which are hereby incorporated by reference in their entirety.

An integrated nanofluidic device was fabricated based on semiconductor device fabrication techniques as described in *Lab on a Chip* 2008, entitled "Monitoring FET Flow Control and Wall Adsorption of Charged Fluorescent Dye Molecules in Nanochannels Integrated into a Multiple Internal Reflection Infrared Waveguide," which is hereby incorporated by reference in its entirety.

In this example, the separation platform of the nanofluidic device had seven nanochannel arrays with each array having a width of about 50 μm and a length of about 14 mm formed on a rectangular Si substrate. The substrate had a width of about 1 cm and a length of about 5 cm. Each nanochannel array of the device included approximately a hundred twenty parallel nanochannels. The dimensions of each nanochannel were about 100 nm width×400 nm depth×14 mm length. Nanochannels were fabricated using interferometric lithography (IL) and plasma etching of Si. A thermally grown $SiO_2$ layer (~100 nm) was used as an electrically insulating layer between Si nanochannel walls and the fluid. The nanochannels were sealed with a Pyrex cover by anodic bonding to form the nanofluidic device.

Optical transparency through the anodically bonded Pyrex cover allowed access to laser-scanning confocal fluorescence microscopy [LS-CFM, Zeiss Axioskop (Chester, Va.) with an LSM5 scanning head] from the top, while IR-transparency through the Si substrate with beveled edges allowed access to multiple-internal reflection Fourier transform infrared spectroscopy (MIR-FTIRS, Nicolet 870 with a mid-IR HgCdTe detector).

Example 2

System Equilibrium

The solution reservoirs (i.e., end wells) and nanochannels were first filled completely with a buffer solution by capillary force. Approximately 30 minutes lapsed before the system reached equilibrium between the buffer solution and $SiO_2$ channel walls. This was based on an observation that no noticeable changes were detected in IR absorbance spectra after 30 minutes. A mixture of proteins was then introduced to one of the wells (as an inlet), and a platinum wire was inserted into each well as an electrode. An electric potential (V) was applied to the protein-containing well, while grounding the other well to create a longitudinal electric field (E) along the nanochannels and to induce an electroosmotic (EO) flow typically with opposing electrophoresis (EP) for negatively charged molecules and to create a longitudinal pH gradient by electrolysis occurring at the electrodes.

Example 3

Buffers and Proteins

Sodium phosphate buffer was used in the exemplary experiments with a buffer pH of 7.2 and an ionic strength of 10 mM. All proteins were diluted to ~0.02 μg/mL in the buffer solution in experiments.

Various exemplary proteins were used as examples. Allophycocyanin (APC), r-phycoerythrin (RPE), bovine serum albumin (BSA) conjugated with Alexa Fluor® 488, and ovalbumin (OVA) conjugated with Alexa Fluor® 555 (see Table 1), were purchased from Invitrogen Corporation (Carlsbad, Calif.) and were used as examples for analyzing proteins using the disclosed systems and methods. Green fluorescent proteins (GFPs) were purchased from Upstate Biotechnology (Lake Placid, N.Y.) and were used to represent small proteins with net positive charge. Molecular weights, isoelectric points, net charges, and specifications on fluorescence (i.e., absorbance, emission, and excitation) of the exemplary proteins are summarized in Table 1.

TABLE 1

|  | RPE | APC | GFP | BSA Conjugates | OVA Conjugates |
| --- | --- | --- | --- | --- | --- |
| Isoelectric Point | 5.1~4.2 | 4.8~4.95 | 5.67 | 4.47~4.85 | 4.43 |
| Molecular Weight | 240,000 | 104,000 | 30,000 | 66,000 | 45,000 |
| Abs(nm) | 480, 546, 565 | 650 | 515 |  |  |
| EM(nm) | 578 | 660 | 509 | 519 | 519 |
| EX(nm) | 568-590 | 633 | 488 | 488 | 555 |
| Net charge | Negative | Negative | Positive | Negative | Negative |

Example 4

Protein Focusing of BSA and OVA

Protein focusing was conducted with an exemplary mixture of BSA ($I_P$=4.47~4.85) and OVA ($I_P$=4.43). BSA and OVA are small proteins with sizes slightly different and are all with net negative charges.

In this example, a time series of schematic images from the BSA/OVA mixture was observed by LS-CFM in one of the seven nanochannel arrays. The BSA/OVA mixture can include protein BSA-Alexa Fluor® 488 conjugates with $EM_{BSA}$=488 and protein OVA-Alexa Fluor® 555 conjugates with $EM_{OVA}$=567. A negative potential, $V_{EP}$=−5, was applied to the inlet well (a right well as shown in FIGS. 2C-2E) in which proteins were introduced.

As observed, for about 36 minutes after the electric potential was applied, proteins were not detected in the nanochannels. This is because electroosmosis flow from left to right was strongly dominant than electrophoresis in nanochannels. In the 37$^{th}$ minute, however, OVA was appeared and focused near the inlet well forming a very sharp band of ~5 μm in width. Later, a band of BSA was focused close to OVA band at the 50$^{th}$ minute.

As also observed, BSA repeatably advanced ahead of OVA from the inlet well in all experiments. The high-resolution focusing of these two proteins continued for about 15 minutes. Then, two bands flowed at 1 μm/s by electrophoresis and became dispersed after traversing 2 mm from the inlet well. Proteins may pass through their isoelectric point due to electrophoresis.

Example 5

Repeatable High-Resolution Protein Focusing of BSA and OVA

The high-resolution protein focusing of BSA and OVA in nanochannels was repeatable. The high-resolution focusing of these two proteins was monitored and demonstrated once again by increasing the electric potential ($V_{EP}$). A time-series snap shots of electrokinetic flow and high-resolution focusing of BSA and OVA were also observed when the electric potential ($V_{EP}$) magnitude was increased from −5 to −10 V. The time-series snap shots were taken every 2 minutes. Note that a portion of proteins was randomly dispersed in nanochannels since they previously flowed from right to left by electrophoresis (see Example 4). Upon applying −10 $V_{EP}$, BSA and OVA quickly flowed back towards the inlet well at 7.3 μm/s for 6 minutes. This flow was induced because the increased electric potential breaks electrokinetic equilibrium and makes the electroosmosis flow from left to right more dominant than electrophoresis. However, as observed, BSA was focused forming a sharp band in 8 minutes. The formation of OVA band followed in 10 minutes.

In this Example 5, the focused band position was 300 μm from the inlet well, which is farther than the distance observed from the lower electric potential ($V_{EP}$=−5) in Example 4. This indicates that the isoelectric points of proteins moved farther into the nanochannels as the pH gradient changed due to the higher magnitude of electric potential (−10 $V_{EP}$). After stationary focusing of the two proteins for about 12 minutes, they flowed farther into the nanochannels at 0.3 μm/s for 12 minutes.

Upon continuous biasing, the two proteins started to flow again from right to left and became dispersed after flowing approximately 3 mm from the inlet well. This result was consistent with the results shown in Example 4. However, a sharp band of OVA and a portion of BSA were observed remaining in the nanochannels. While not desiring to be bound by any particular theory, this may have been caused by: (1) adsorption of proteins to the nanochannel walls or (2) continuous protein focusing after most of the proteins have moved out of their isoelectric point by electrophoresis.

Example 6

Protein Separations

To achieve clear band separation of proteins, a protein mixture including BSA, OVA, RPE, APC, and GFP were used in various combinations. As a result, in the range of electric potential from −5 to −40 $V_{EP}$, BSA and OVA always appeared and formed sharp bands. In contrast, RPE, APC, and GFP did not form bands until the electric potential was raised to −40 $V_{EP}$. However, upon applying −60 $V_{EP}$, RPE and APC both appeared forming sharp bands near the inlet well, while GFP still did not appear in the nanochannels.

GFP (MW~30,000) was not shown in the range of electric field ($V_{EP}$=−5~−60) as studied here, although the molecular size was the smallest. This phenomenon is likely due to the electrostatic charge interaction of charged GFP and the cathode, where native pH value decreases in nanochannels due to deprotonation of hydroxyl groups on the channels walls. Therefore, the pH value in the nanochannel was estimated to be approximately 6 at which GFP was positively charged, while positively charged GFP did not flow into the nanochannels as long as the negative potential was applied to the inlet electrode (the cathode).

In experiments, BSA was observed to have a higher mobility than OVA and this mobility difference was used for separation. Various experiments also included focusing and separation of BSA and OVA by modulating the magnitude of the electric potential ($V_{EP}$) from −20 to −40 V.

As observed in the particular experiment, band formations of BSA and OVA were achieved in 5 minutes upon applying an electric potential of about −40 $V_{EP}$. This band formation occurred more quickly than in the case of using a low electric potential ($V_{EP}$). These band formations continued for 8 minutes. When the electric potential magnitude was lowered to −20 $V_{EP}$, these bands quickly moved from right to left (e.g., from the 10$^{th}$ minute to the 18$^{th}$ minute) at 60 μm/s. That is, the low-magnitude (−20V) weakened the electroosmosis flow, inducing bands of proteins move from right to left. The protein bands again moved back towards the inlet upon raising the electric potential magnitude to −40 $V_{EP}$, and again its direction reversed upon lowering the magnitude to −20 $V_{EP}$. This observation was highly repeatable. The other significant phenomenon observed meanwhile was a separation of BSA and OVA. Upon lowering the electric potential magnitude to −20 $V_{EP}$, BSA completely moved back to the inlet, whereas OVA was still focused and remained at the same position.

While the invention has been illustrated with respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for focusing proteins comprising:
providing a plurality of nanofluidic channels, wherein one of a width and a depth of each nanofluidic channel is about 1000 nm or less;
equilibrating a buffer solution with walls of the plurality of nanofluidic channels suitable for the proteins to be focused by determining an equilibrium time by IR absorbance spectra;
introducing a protein mixture solution that contains a plurality of proteins into the nanofluidic channels; and
applying an electric potential to a length of the protein mixture solution along the nanofluidic channels to generate a longitudinal electric field.

2. The method of claim 1, further comprising forming at least one focused protein band by the longitudinal electric field, wherein the at least one focused protein band has a width of about 100 micrometers or less.

3. The method of claim 2, wherein the at least one focused protein band is statically focused for a period of time ranging from about 5 minutes to about 30 minutes.

4. The method of claim 2 further comprising advancing a location of the at least one focused protein band further along the nanofluidic channels by increasing the applied electric potential.

5. The method of claim 1, wherein the protein mixture solution has a protein concentration of about 1 millimolar or less.

6. The method of claim 1 further comprising separating the plurality of proteins in the protein mixture solution using one or more of isoelectric focusing (IEF), dynamic field gradient focusing (DFGF) and a combination thereof.

7. The method of claim 1 further comprising applying a low electric potential of about 5 V or less for isoelectric focusing (IEF) the plurality of proteins in the protein mixture solution.

8. The method of claim 1 further comprising:
filling the buffer solution into the plurality of nanofluidic channels, and
equilibrating the buffer solution with walls of the plurality of nanofluidic channels.

9. The method of claim 1 further comprising increasing the applied electric potential to reduce a band formation time from the application of the electric potential.

10. The method of claim 1 further comprising determining and applying a high electric potential to generate the longitudinal electric field when the plurality of proteins in the protein mixture solution have a high molecular weight.

11. The method of claim 1 further comprising changing the electric potential applied to the protein mixture solution to change a flowing direction of the plurality of proteins along the nanofluidic channels.

12. The method of claim 1 further comprising separating a plurality of proteins with sizes in the same range.

13. The method of claim 1 further comprising configuring a multi-gate nanofluidic field-effect-transistor (FET) having a plurality of gates spaced along the nanofluidic channels.

14. The method of claim 13 further comprising applying a second electric potential through the plurality of gates of the multi-gate nanofluidic FET to dynamically control at least one of a pH gradient, an electric field gradient and electrokinetic transport of the plurality of proteins in the nanofluidic channels.

* * * * *